(12) United States Patent
Hale et al.

(10) Patent No.: US 9,603,508 B2
(45) Date of Patent: *Mar. 28, 2017

(54) METHOD FOR CAPTURING AND DISPLAYING ENDOSCOPIC MAPS

(75) Inventors: Eric Lawrence Hale, Altadena, CA (US); Hans David Hoeg, Arcadia, CA (US); Nathan Jon Schara, Pasadena, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1579 days.

This patent is subject to a terminal disclaimer.

(21) Appl. No.: 12/015,222

(22) Filed: Jan. 16, 2008

(65) Prior Publication Data
US 2008/0161642 A1 Jul. 3, 2008

Related U.S. Application Data

(63) Continuation of application No. 10/829,767, filed on Apr. 21, 2004, now Pat. No. 7,381,183.

(60) Provisional application No. 60/464,085, filed on Apr. 21, 2003.

(51) Int. Cl.
| *A61B 1/04* | (2006.01) |
| *A61B 1/00* | (2006.01) |
| *A61B 1/06* | (2006.01) |

(52) U.S. Cl.
CPC ........ *A61B 1/00183* (2013.01); *A61B 1/0005* (2013.01); *A61B 1/00009* (2013.01)

(58) Field of Classification Search
USPC ........ 600/117, 145, 170, 171, 173, 103, 109
See application file for complete search history.

(56) References Cited

U.S. PATENT DOCUMENTS

| | | |
|---|---|---|
| 3,856,000 A | 12/1974 | Chikama |
| 3,880,148 A | 4/1975 | Kanehira et al. |
| 4,697,577 A | 10/1987 | Forkner |
| 5,243,967 A | 9/1993 | Hibino |
| 5,257,618 A | 11/1993 | Kondo |
| 5,262,867 A | 11/1993 | Kojima |
| 5,313,306 A | 5/1994 | Kuban et al. |
| 5,776,050 A | 7/1998 | Chen et al. |
| 5,800,341 A | 9/1998 | McKenna et al. |
| 6,035,229 A * | 3/2000 | Silverstein et al. .......... 600/473 |
| 6,364,830 B1 | 4/2002 | Durell |
| 6,371,909 B1 | 4/2002 | Hoeg et al. |
| 6,443,894 B1 | 9/2002 | Sumanaweera et al. |
| 6,449,103 B1 | 9/2002 | Charles |

(Continued)

*Primary Examiner* — Anhtuan T Nguyen
*Assistant Examiner* — Alexandra Newton
(74) *Attorney, Agent, or Firm* — Whitmyer IP Group LLC

(57) ABSTRACT

A method for capturing and displaying endoscopic maps is disclosed generally comprising providing an endoscope with a view vector that pivots relative to the longitudinal axis of the endoscope, programming a scan trajectory along which the view vector moves relative to the longitudinal axis of the endoscope to provide a predefined sequence of views of a surface, and capturing a sequence of images corresponding to the predefined sequence of views as the view vector moves along that scan trajectory. A set of configuration coordinates is associated with each of the captured images, and the images and the coordinates associated therewith are used to create a map of the interior surface that is larger than the view attending the view vector.

21 Claims, 16 Drawing Sheets

(56) References Cited

U.S. PATENT DOCUMENTS

| | | | |
|---|---|---|---|
| 6,500,115 B2 | 12/2002 | Krattiger et al. | |
| 6,663,559 B2 | 12/2003 | Hale et al. | |
| 6,671,581 B2 | 12/2003 | Niemeyer et al. | |
| 7,029,436 B2 * | 4/2006 | Iizuka et al. | 600/160 |
| 2002/0103420 A1 | 8/2002 | Coleman et al. | |
| 2002/0181802 A1 | 12/2002 | Peterson | |
| 2003/0018235 A1 | 1/2003 | Chen et al. | |
| 2003/0220541 A1 * | 11/2003 | Salisbury et al. | 600/101 |
| 2004/0220478 A1 * | 11/2004 | Wallace et al. | 600/476 |

* cited by examiner

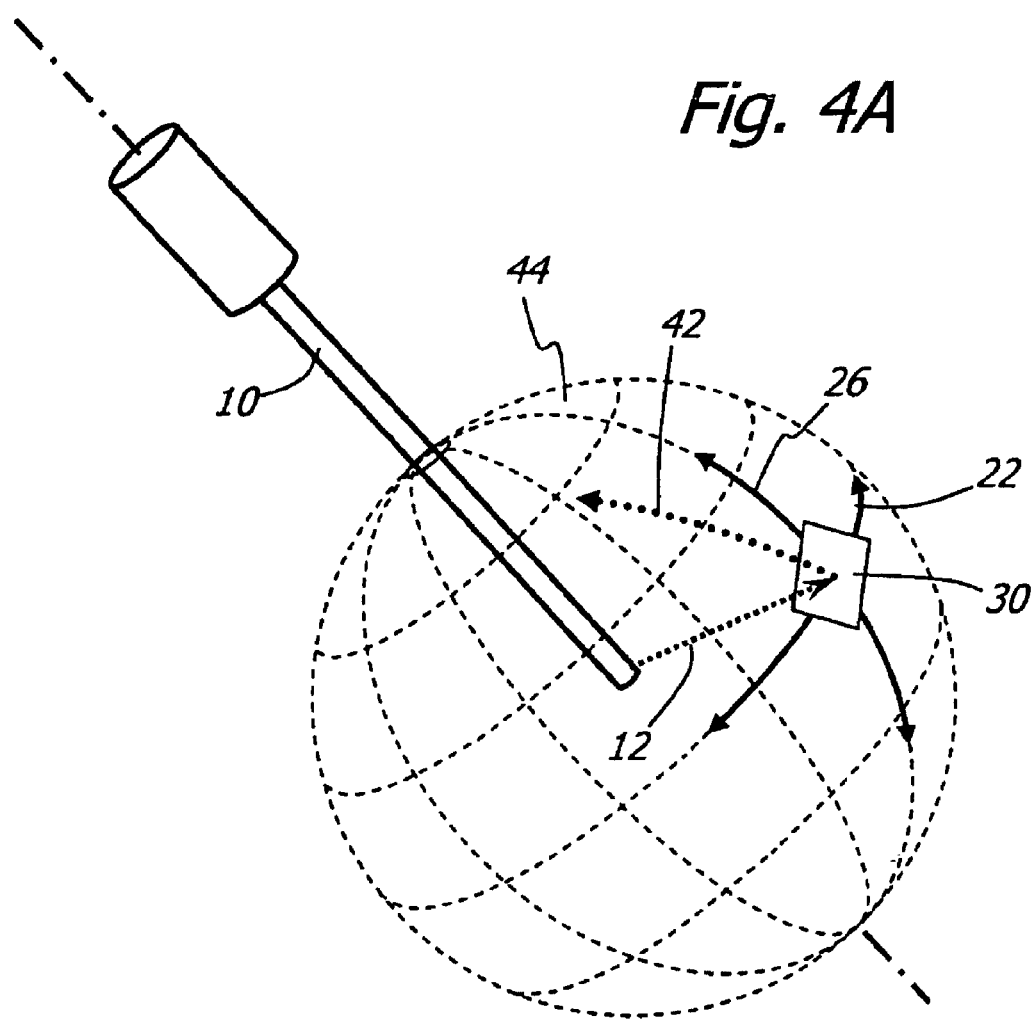

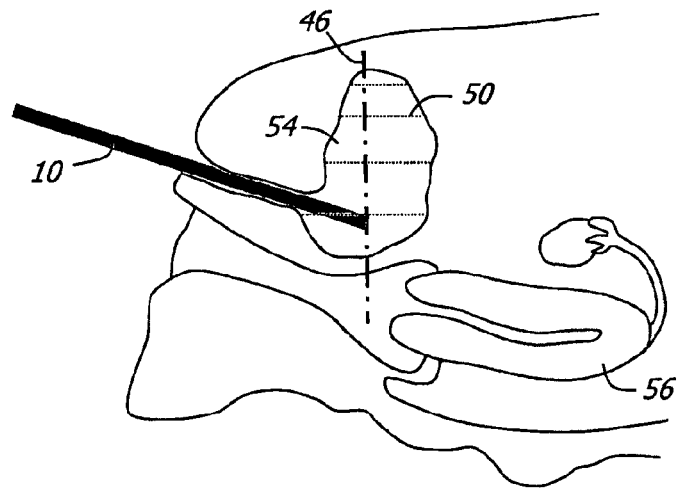
*Fig. 6A*
*Fig. 6B*
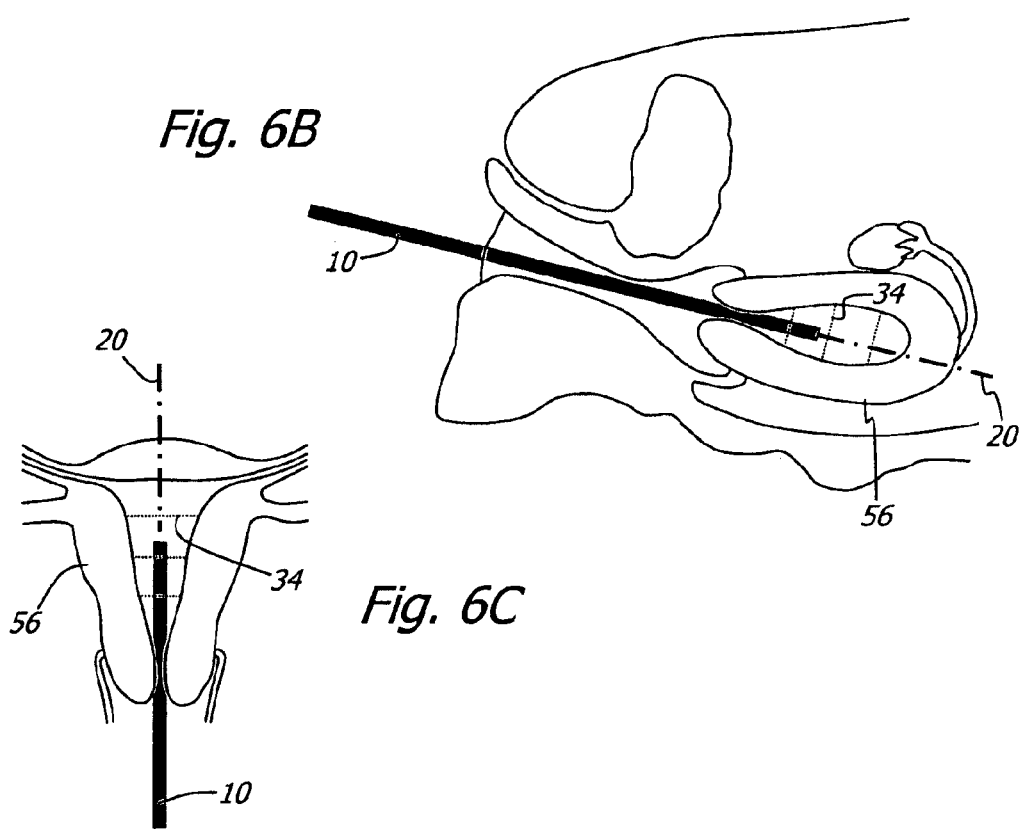
*Fig. 6C*

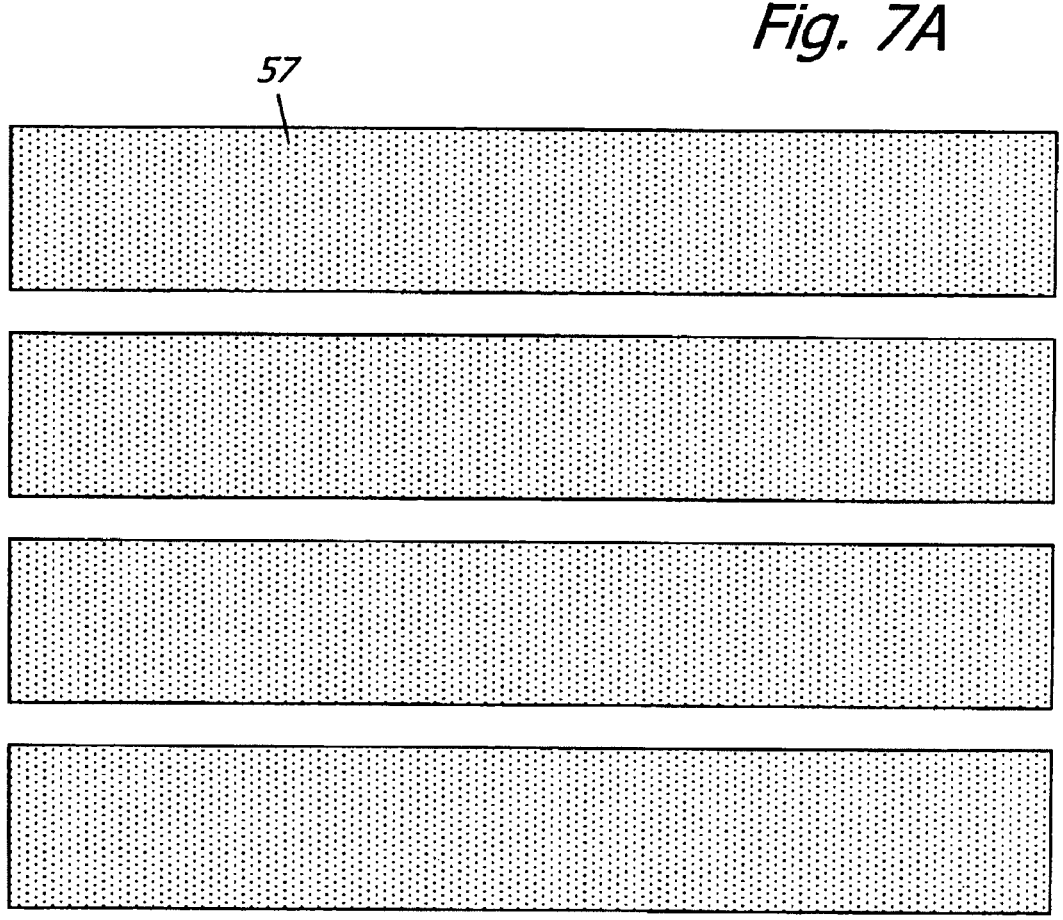

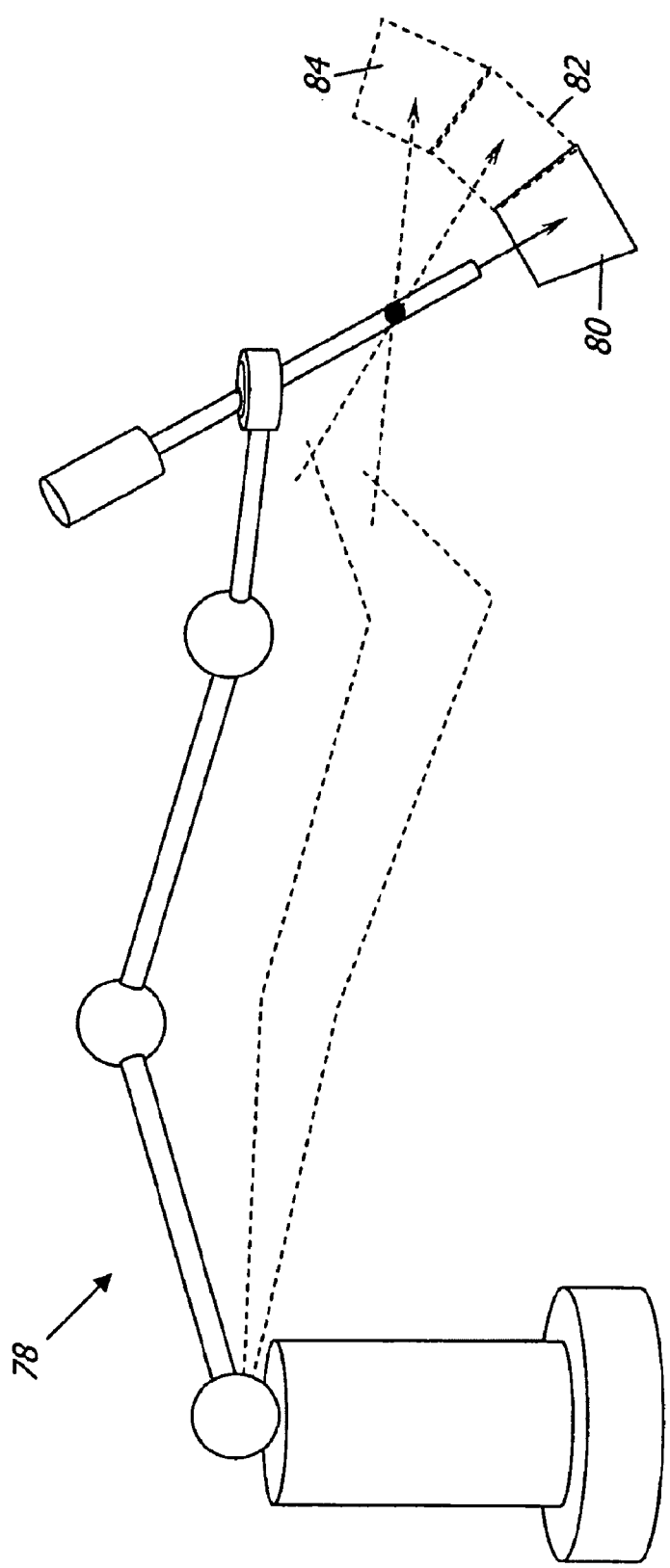

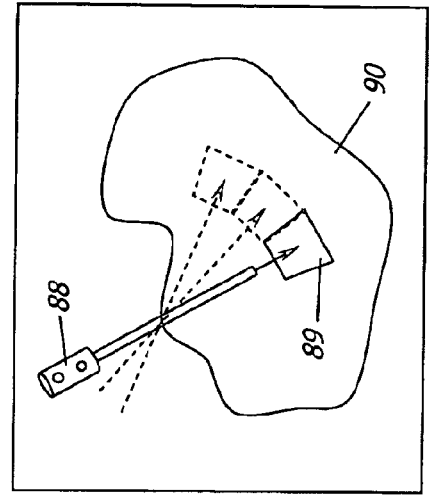
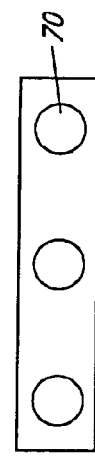
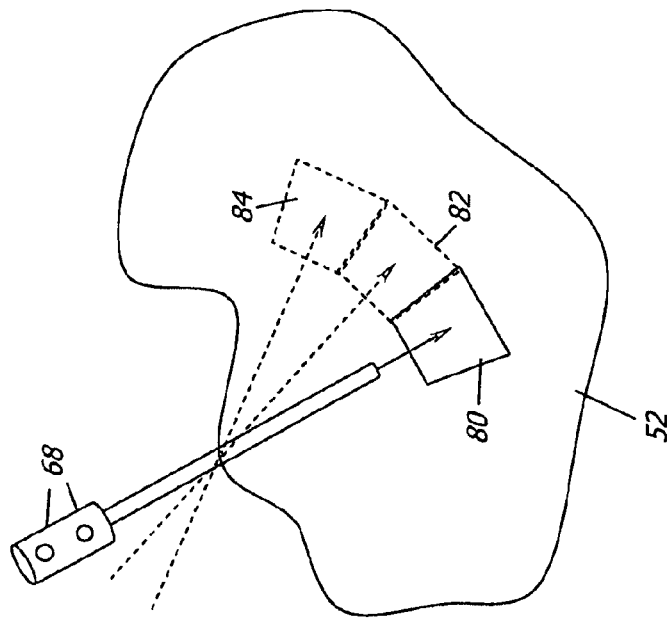

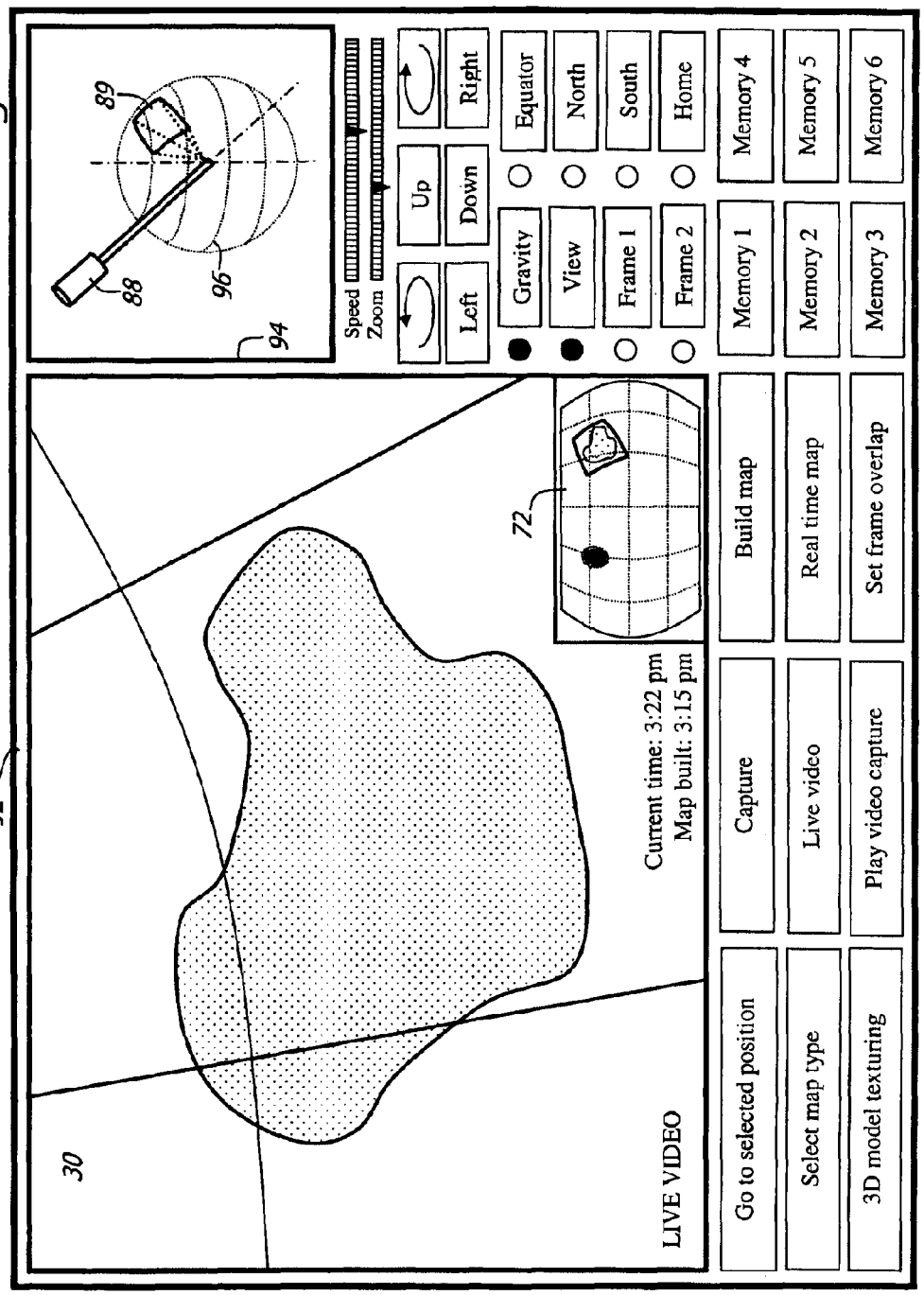

METHOD FOR CAPTURING AND DISPLAYING ENDOSCOPIC MAPS

CROSS-REFERENCE TO RELATED APPLICATIONS

This application is a continuation of U.S. patent application Ser. No. 10/829,767, filed Apr. 21, 2004, which application is currently pending and which application claims the benefit of U.S. provisional application Ser. No. 60/464,085 filed Apr. 21, 2003, entitled "Methods for capturing, building, and displaying endoscopic maps," the contents of which are incorporated herein by reference.

FIELD OF THE INVENTION

The present invention relates to endoscopic diagnosis.

BACKGROUND OF THE INVENTION

The present invention is based on two fundamental premises: i) effectively curing malignancy such as cancer depends early detection, which has two elements: sufficient image resolution to identify small lesions and tumors, and sufficient and reliable viewing coverage to ensure there are no diagnostic blind spots; and ii) because viewing is limited, current endoscopic diagnostic procedures can be time consuming and require substantial training. For example, the main challenge in cystoscopic screening of bladder cancer is ensuring that the diagnosis reliably covers the entire interior bladder surface.

Being able to obtain high-resolution wide-angle endoscopic maps would be useful in diagnosis, surgical planning, surgical intervention, and post-surgical diagnosis for verifying tumor removal. Particular utility would be in cystoscopic cancer screening, hysteroscopic diagnosis of the interior surface of the uterus (National Institute of Health Grant No. 1R43CA097824-01), imaging of the nose and throat cavities, and neuroendoscopy of the brain's ventricular system where it is very easy to get disoriented and where it is important to minimize gross instrument motion. Further applications include arthroscopy for imaging of joint cavities, and endoscopic inspection of the thorax.

Current technology is limited in its ability to provide both high resolution and wide reliable viewing coverage in a single system. Noninvasive imaging techniques such as X-ray, MRI, CT, ultrasound, and their derivative virtual endoscopy, have unlimited viewing directionality and the positioning accuracy necessary for building complete diagnostic maps of the anatomy, but their imaging resolution is an order of magnitude less than that of endoscopy. Currently these methods are only able to resolve mature tumors several millimeters in diameter, and improving this resolution is still going to require prolonged scientific development. It is also unlikely that these techniques will ever be able to identify tissue color, which is important in diagnosis.

Conversely, endoscopic imaging has excellent optical resolution and color information but is plagued by inconsistencies in viewing coverage. The endoscopic viewing process is hampered by a limited field of view and is mechanically constrained by the endoscope insertion port and interior anatomy. It is further complicated by the fact that the endoscope provides no natural sense of orientation, and it is common for an operator to get lost or disoriented while using endoscopes. Getting reliable diagnoses with endoscopes is therefore operator dependent, and there is great variability in the skill levels of endoscopists. Obtaining a structured sense of the surroundings requires the endoscopist to cover all areas of an inspection site and to keep a mental record of the relative endoscopic viewing positions. It also requires that the endoscopist distinguish between regions already covered and regions not yet inspected (much like to trying to ensure complete coverage when vacuuming the floor). These tasks require great technical skill, spatial awareness, and memory and are so challenging that endoscopic diagnoses often leave missed areas.

One of the underlying problems here is that endoscopic diagnosis is generally a free-hand technique. Whether the diagnosis is being performed with a fixed-angle endoscope, a flexible variable direction of view scope (U.S. Pat. No. 3,880,148 to Kanehira, U.S. Pat. No. 5,257,618 to Kondo), or a rigid variable direction of view scope (U.S. Pat. No. 3,856,000 to Chikama, U.S. Pat. No. 4,697,577 to Forkner, U.S. Pat. No. 6,371,909 to H.o slashed.eg et al., U.S. Pat. No. 6,364,830 to Durell, U.S. Pat. No. 6,500,115 to Krattiger et al.), or a hybrid scope, (the LTF TYPE V3 Olympus Laparo-Thoraco Videoendoscope in which the main shaft is rigid but the tip portion can be flexed), it is subject to the inconsistencies of manual endoscope manipulation with no means for doing accurate position registration between views. The VOCAL (Video Optical Comparison and Logging) software package somewhat improves this situation by recording running video of endoscopic procedures and integrating sequential frames into composite images. This provides the user with a broader diagnostic overview but does not address the problem of discontinuous coverage and missed areas and also does not yield accurate information about the relative location of viewed areas.

Other attempts to minimize diagnostic inconsistencies are disclosed in U.S. Pat. No. 5,313,306 to Kuban et al., U.S. Pat. No. 6,449,103 to Charles, and U.S. Pat. No. 5,800,341 to McKenna et al. These designs propose to capture panoramic or omniramic imaging information in a single large frame and avoid the problem of having to mentally patch together disjoint view fields. While good in concept, these designs can not currently provide sufficient resolution and illumination and have apparently never been reduced to practice.

Accordingly, the current invention provides a method for capturing composite endoscopic images. This method will improve endoscopic diagnosis by providing accurate high-resolution low-distortion wide-angle visual coverage; obtaining panoramic and omniramic information by automated capture; building and displaying composite images of the endoscopic space with minimal blind spots; minimizing user disorientation; and reducing procedure time. Other advantages will become apparent from the following.

SUMMARY OF THE INVENTION

In accordance with the present invention, a method is provided for capturing and displaying endoscopic maps.

BRIEF DESCRIPTION OF THE DRAWINGS

FIGS. 4A, 4B and 4C illustrate off-axis and helical scanning.

FIGS. 6A, 6B and 6C illustrate cystoscopic and hysteroscopic applications.

FIGS. 7A, 7B, 7C, 7D, and 7E illustrate the concept of creating a composite image/map out of scan sequences or individual frames.

FIGS. 10A and 10B show capturing endoscopic maps with a robotically manipulated endoscope and a fixed-angle side-viewing endoscope, respectively.

FIGS. 11A and 11B illustrate manual image guided endoscopic mapping.

FIG. 12 shows a GUI for managing an endoscopic mapping system.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

An endoscope map will be defined as a composite or compound image created from more than one individual frame. Such a composite image can be a set of individual frames such as a mosaic or a single contiguous integrated field synthesized from individual frames.

PREFERRED EMBODIMENT

Figure 1:
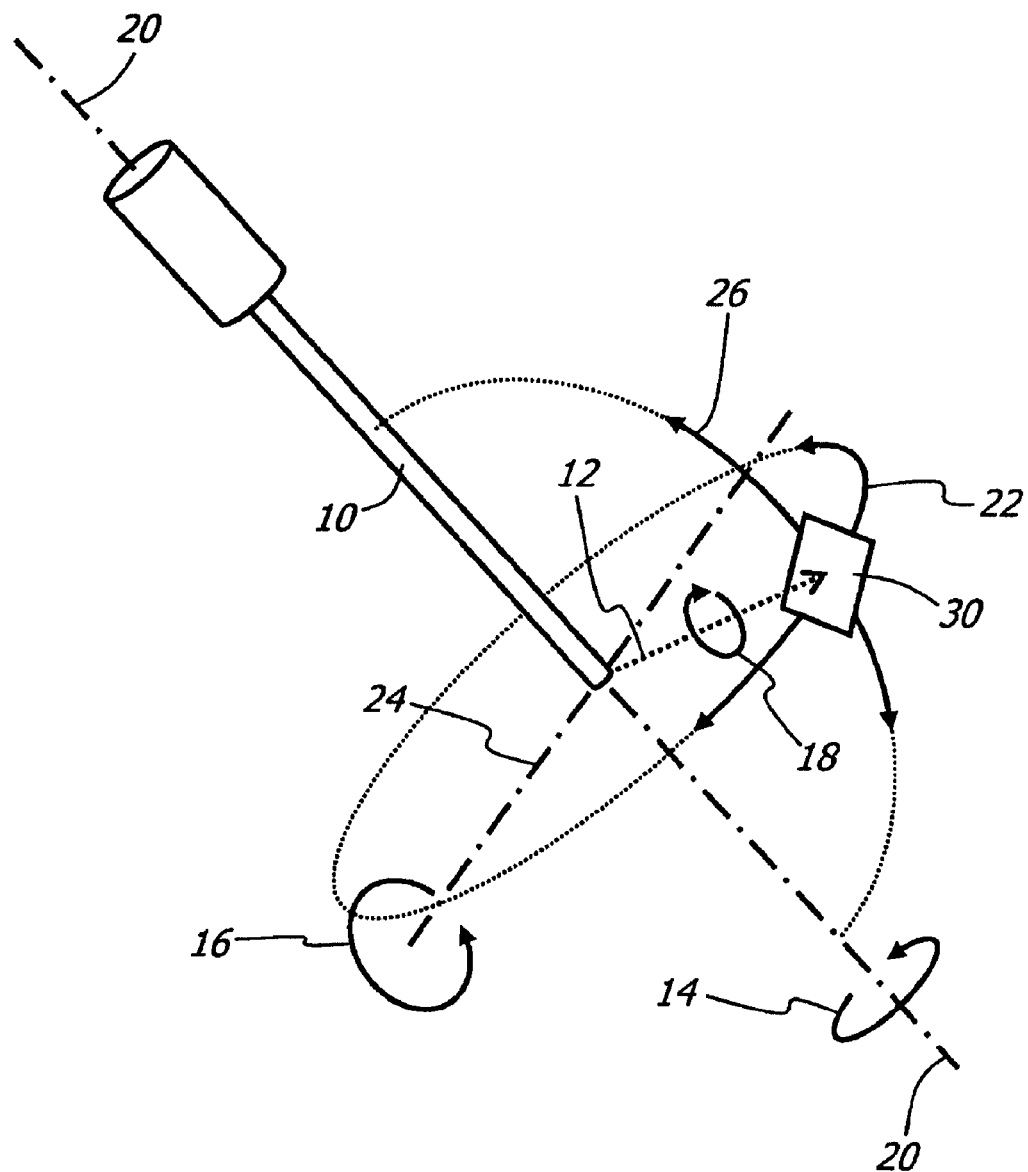
FIG. 1 shows the operating principle of a typical rigid variable direction endoscope.

Referring now to the drawings, in which like reference numbers represent similar or identical structures throughout, FIG. 1A is a diagram of a basic variable direction of view endoscope 10. Such an endoscope typically has a view vector 12 with at least two degrees of freedom 14, 16. The first degree of freedom 14 permits rotation of the view vector 12 about the longitudinal axis 20, which allows the view vector 12 to scan in a latitudinal direction 22. The second degree of freedom 16 permits rotation of the view vector 12 about an axis 24 perpendicular to the longitudinal axis 20, which allows the view vector 12 to scan in a longitudinal direction 26. These degrees of freedom define a natural endoscope coordinate system. A third degree of freedom 18 may also be available because it is usually possible to adjust the rotational orientation of the endoscopic view frame 30.

Figure 2A:
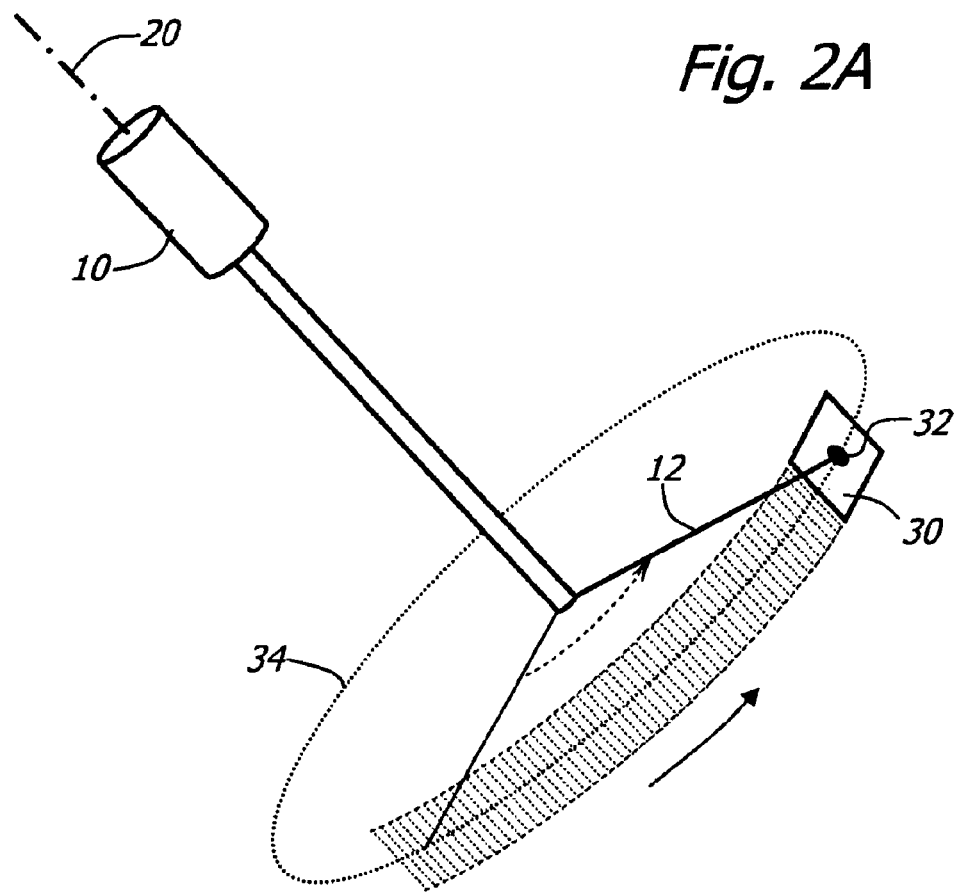
FIGS. 2A and 2B show the principle of latitudinal endoscopic scan with streaming video and tiled frames.
Figure 2B:
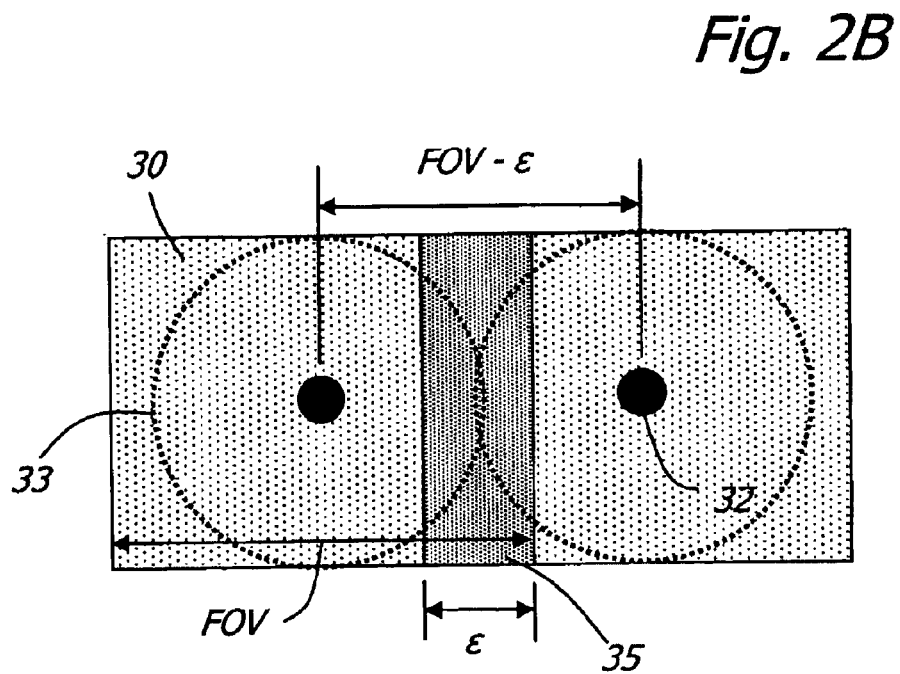

U.S. Pat. No. 6,663,559 to Hale et al. discusses an endoscope control interface which enables electronic position control of a variable direction of endoscope. With this interface, or other electromechanical position control, relative registration between endoscopic views is possible, and the endoscopic view vector 12 can be programmed to follow preset viewing sequences or trajectories. A scan trajectory will be defined as the locus of the center of the endoscopic view frame 30. Each view frame 30, or set of frames, captured along a trajectory is identified by a set of endoscope configuration coordinates representing the states of the three degrees of freedom. These coordinates are stored in a frame-indexing array which correlates visual information with viewing position. FIG. 2A shows the principle of collecting visual information from a latitudinal trajectory 34. While rotating about its principal axis 20, the endoscope 10 captures video at a certain frame rate. The scanning speed can be adjusted according to the video frame rate and the size and geometry of the frame 30. Successive frames overlap, as shown in FIG. 2B, to ensure seamless coverage, and the overlap 35 can be set by the operator. The area of overlap between adjacent frames 30 depends on the view field geometry. This geometric effect becomes important when planning scan trajectories for obtaining contiguous coverage without gaps or holes, as discussed below. Within this upper bound, the scanning speed can be optimized for the system and the application. For example, systems intended for non-interactive diagnoses (as with radiography where the information is inspected after a complete scan sequence) can have very small fields of view to maximize resolution because the user will be looking at a final composite map rather than individual fields of view, making scanning speeds and processing time less important.

Figure 3A:
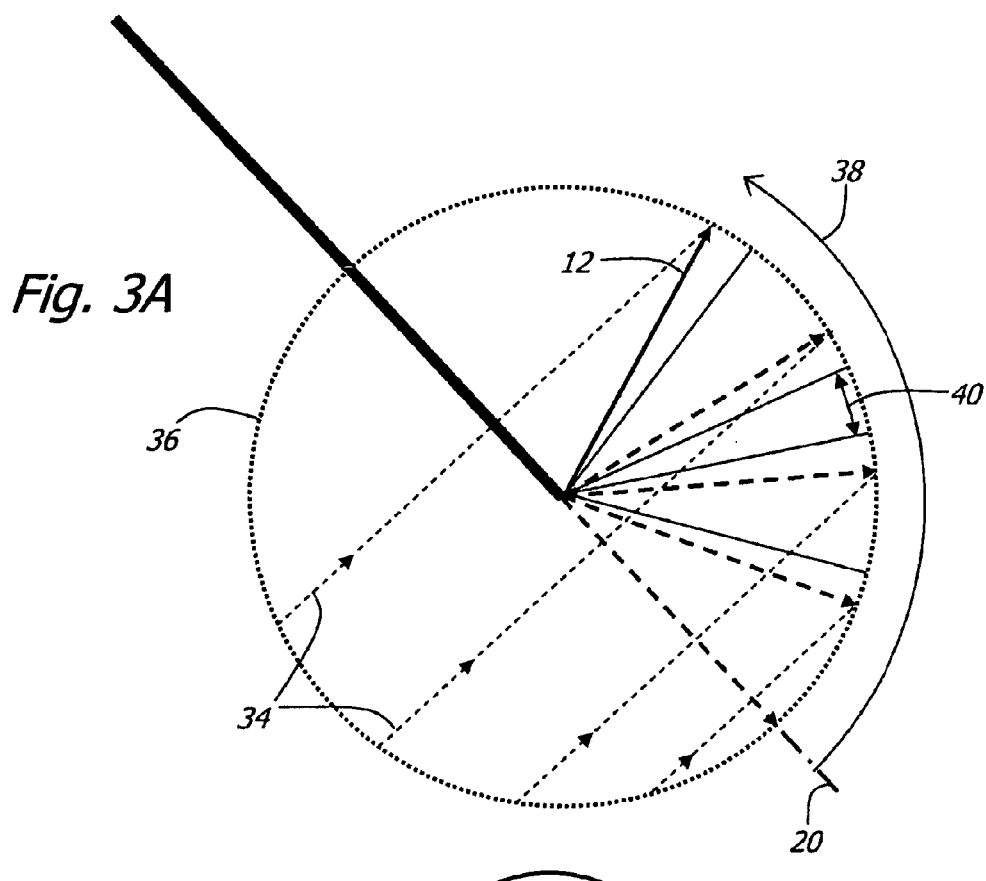
FIGS. 3A and 3B show the concept of omniramic gapless visual coverage.

Systematic scan trajectories make it possible to cover a spherical solid angle 36, as shown in FIG. 3A. For example, by moving the view vector 12 through a longitudinal range 38, multiple latitudinal scans 34 can be stacked to provide wide-angle information (It is important to note that the spherical angle 36 represents the angular mobility range of the mechanism and is unrelated to the actual size and geometry of an anatomical cavity). Each scan 34 overlaps 40 the preceding scan to ensure contiguous visual coverage.

Figure 3B:
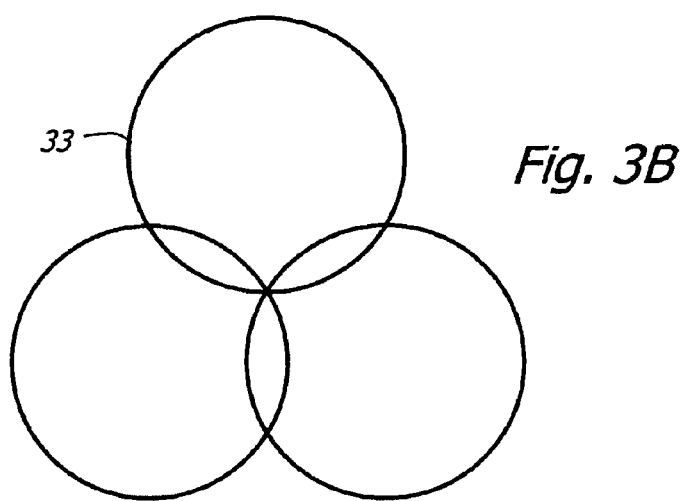

A related way to provide reliable visual coverage scheme is to capture only as many frames as necessary to cover a globe. Rather than executing a continuous scanning motion the mechanism could systematically move to discrete positions and capture a frame in each position. To provide reliable coverage with no gaps, it is necessary to consider the geometry of the view frame 30. Videoendoscopes (endoscopes which have an image sensor at the tip) may have square or rectangular view fields depending on the objective lens arrangement. Squares and rectangles can be systematically tiled to ensure contiguous coverage, and there should be no relative rotation between frames. Most endoscopes however have a circular view field 33, in which case radial symmetry makes field orientation irrelevant. For contiguous coverage with a circular view field, the ideal arrangement of neighboring frames is shown in FIG. 3B.

Figure 4B:
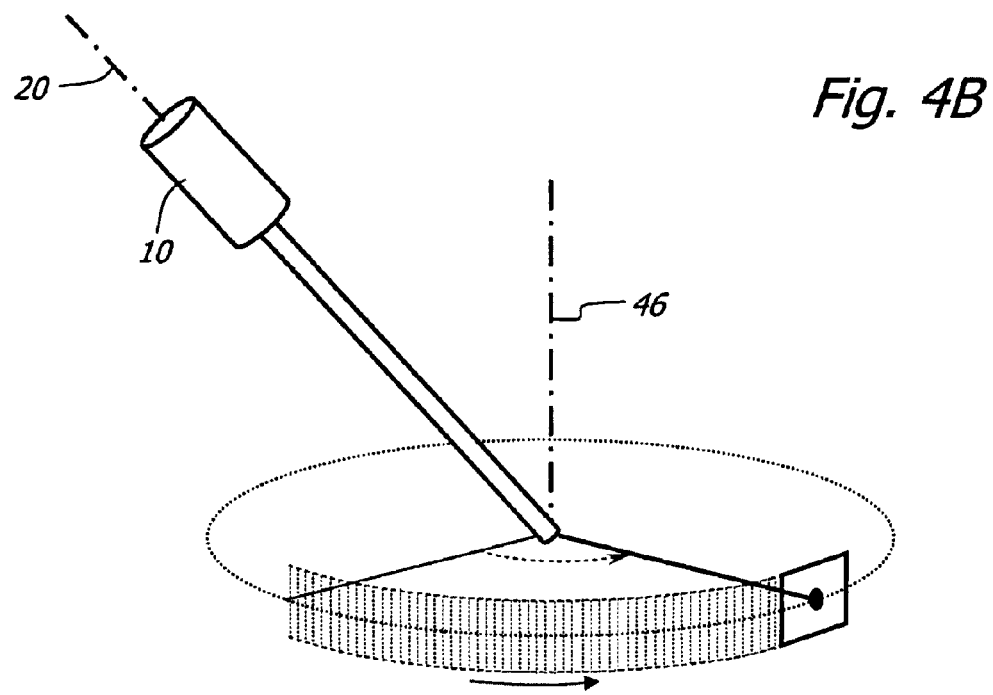
Figure 4C:
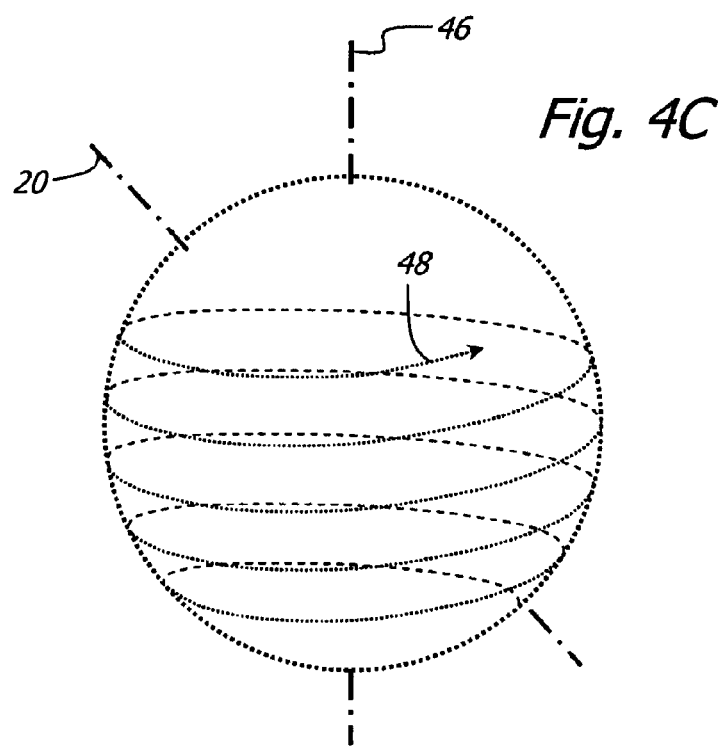

The system described in Hale et al. can combine individual degrees of freedom to generate smooth off-axis view vector movements 42 that are not aligned with the natural frame 44 of the endoscope 10, as shown in FIG. 4A. Because smooth off-axis movements are possible, scans can also be aligned with a virtual axis 46 rather than the mechanical axis 20 of the endoscope 10, as illustrated in FIG. 4B. This can be useful in cases when the user desires a particular orientation relative to the anatomy or gravity. It also becomes possible for the system to perform more complex scans, such as a continuous helical scan 48 which does not require intermittent discrete view vector adjustment, as shown in FIG. 4C. Various scanning sequences and movement combinations are possible without departing from the scope of this invention; for example stacking longitudinal panoramas, or scanning in a reciprocating pattern and patching the scan areas together. The computer can also optimize scan trajectories according to the kinematics and dynamics of the endoscope.

Figure 5A:
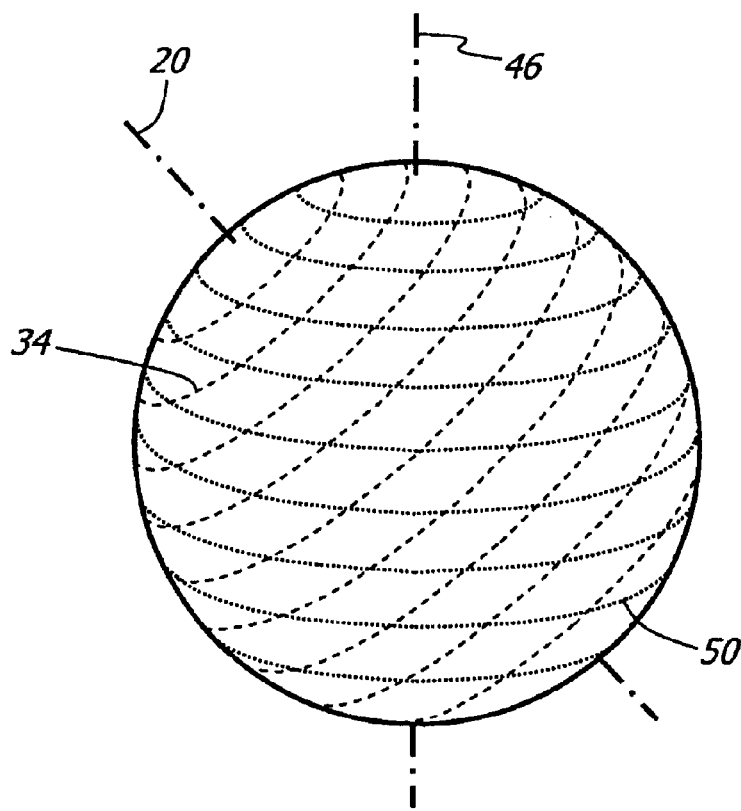
FIGS. 5A and 5B show off-axis latitudinal scanning relative to a designated virtual axis favorably aligned with the anatomy.
Figure 5B:
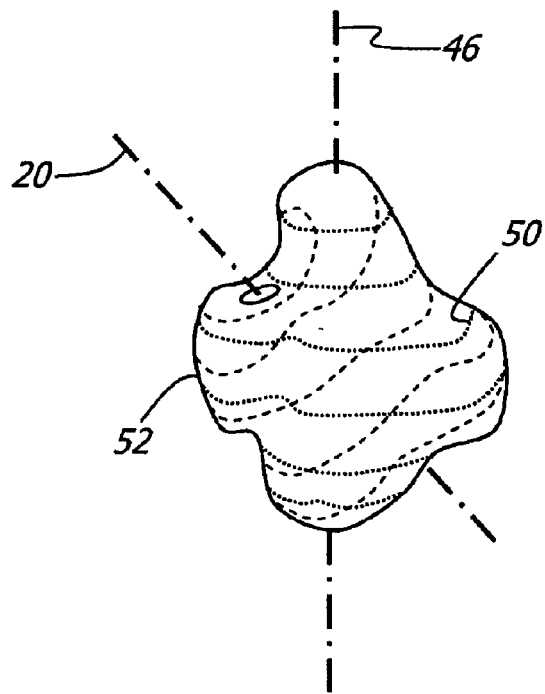

FIG. 5A shows a series of off-axis scans 50 aligned with a virtual axis 46 compounded to cover a spherical solid angle. These scans 50 are shown relative to latitudinal scans 34 aligned with the natural endoscope frame 20. Off-axis scanning can be useful when an anatomical cavity has an inherent directionality or when the user has a personal preference as to how the visual information should be oriented, such as aligned with gravity etc. FIG. 5B shows an anatomical cavity 52 with a natural directionality 46 at an angle to the endoscope insertion axis 20. The scans 50 are aligned with the axis 46 to help the user to stay oriented during diagnosis or surgery. If the user is watching the diagnosis in real time, locally or remotely, the image orientation is important. If the user is to perform a non-interactive diagnosis, for example in her office after-an automated capture has taken place, the mechanical capture pattern and viewing orientation is less important because a map can be reoriented after construction.

Examples of specific applications for the method of the present invention are given in FIGS. 6A, 6B, and 6C, which show standard endoscopic examinations of a bladder 54 (cystoscopy) and a uterus 56 (hysteroscopy). Often these procedures require dilation of the cavity with a fluid or gas in order keep the tissue from being collapsed, such as the uterus 56 in FIG. 6A, and make it possible for an endoscope to view the parietal walls. For cystoscopy, where the endoscope 10 is inserted through the urethra, the surgeon might choose scan lines 50 oriented relative to the direction of gravity 46. For hysteroscopy, the surgeon might prefer to align the diagnosis with the endoscope insertion axis 20. FIG. 6C shows a top section view of the uterus 56.

The simplest way to communicate the captured imaging information to a reviewer is to play back the captured video stream from a continuous helical scan. The reviewer then simply watches the movie and looks for lesions or other tissue abnormalities. This is the current method for reviewing imaging data captured from a gastrointestinal capsule endoscope such as those commercially available from Given Imaging.

Figure 7B:
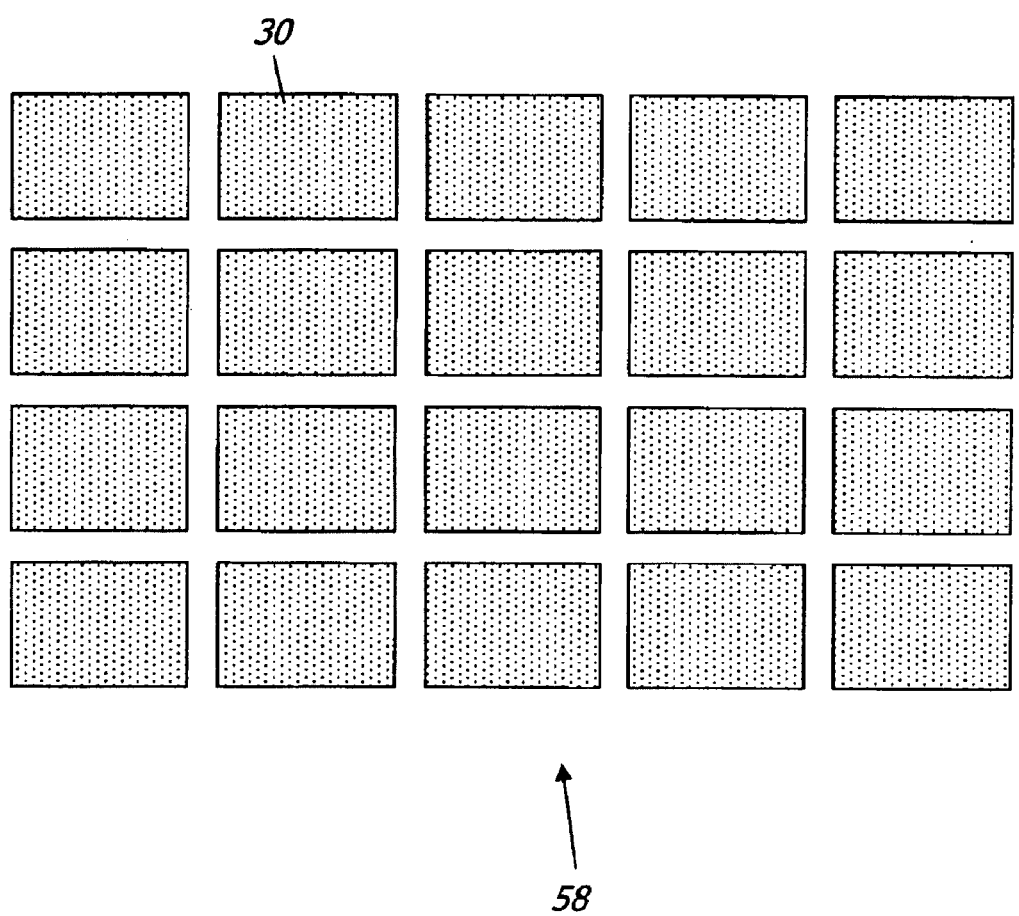

Another way to communicate the imaging information is to display portions of the videostream as still image strips 57 which together provide complete visual coverage of the examined area, as shown in FIG. 7A. A similar technique is to display a mosaic 58 of discrete frames 30, as seen in FIG. 7B.

Figure 7C:
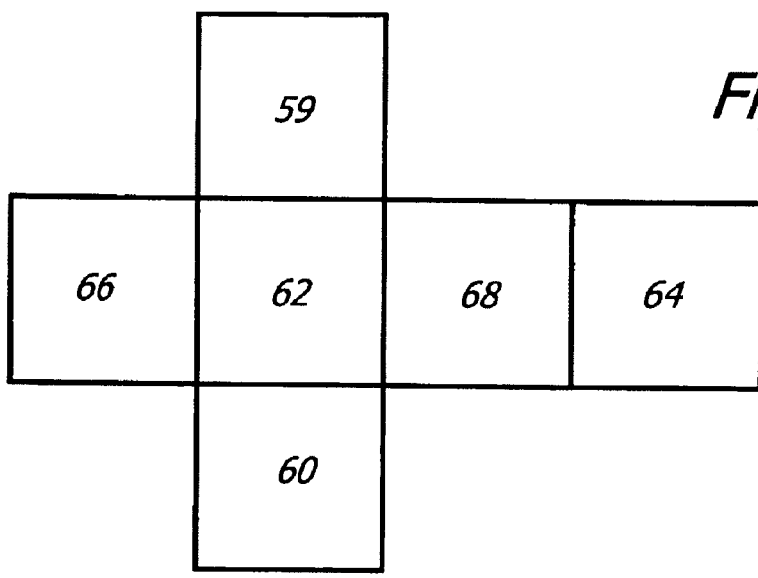
Figure 7D:
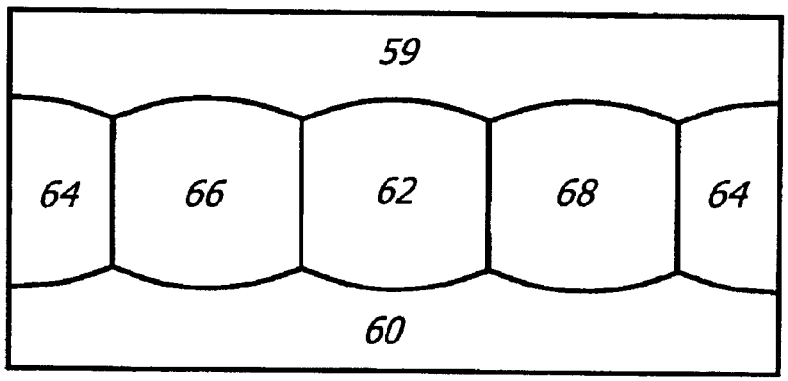
Figure 7E:
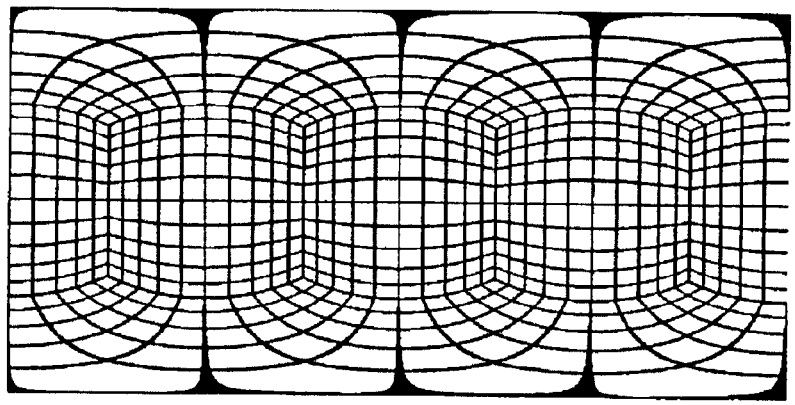

It is also possible to integrate the frames 30 into a contiguous map by stitching them together electronically. There are a number of commercially available pixel filtering and averaging algorithms for generating seamless composites, for example the VOCAL package mentioned above, or the VideoFOCUS software which processes sequential video frames in order to produce a single high-quality image. In presenting an assembled map to the user, a number of different mapping formats can be used. Which cartographic projection scheme to use depends on the type of information the map is intended to accentuate. Conformal mappings preserve local angles in the projection. This type of map is good for local view vector movements. Equal area mappings map areas on a sphere or other appropriate object to equal or scaled areas in the plane. This type of map is good for comparing sizes of lesions or tumors on different areas of the map. Equidistant mappings preserve or scale distances. Such mappings are useful for showing optimal paths between points. FIGS. 7C, 7D, and 7E show captures of up 59, down 60, forward 62, backward 64, left 66, and right 68 being assembled into a global map. Some of the straight frame lines in FIG. 7C are distorted into curves in FIGS. 7D and 7E.

Figure 8A:
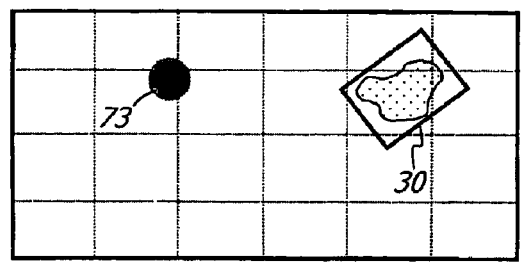
FIGS. 8A, 8B, and 8C show various types of maps.
Figure 8B:
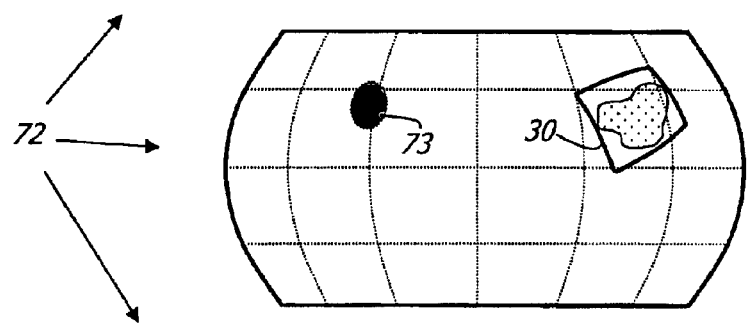
Figure 8C:
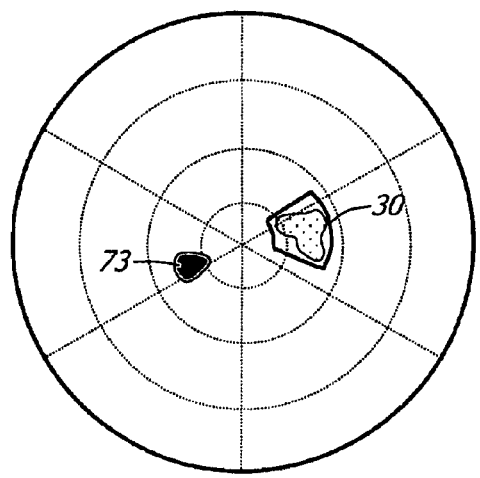

FIGS. 8A, 8B, and 8C respectively illustrate Mercator, Mollweide, and Polar maps 72 with the real time position of the endoscopic view 30 and the endoscopic entry port 73 indicated. The user can also select a position on the map with an input device such as a mouse or a joystick, causing the endoscope to center its view on the selected position. This go-to feature is also an important positioning aid for biopsy or therapy. Any type of mapping is applicable to the present invention.

Figure 9A:
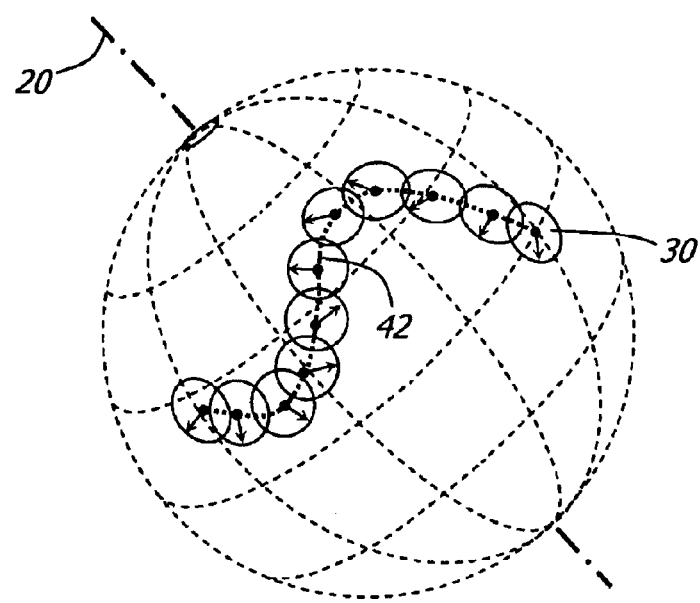
FIGS. 9A and 9B show the concept of running map generation and continuous updating.
Figure 9B:
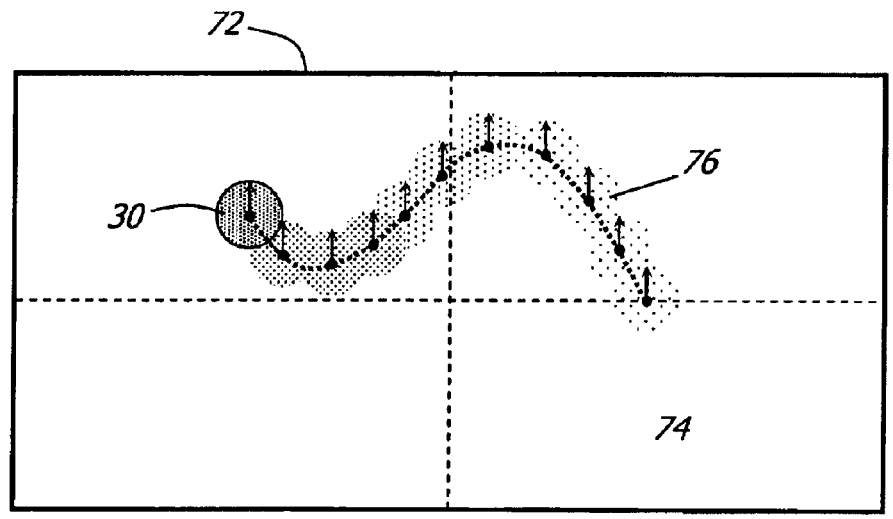

During a diagnosis or surgical procedure, a user may move through a random trajectory 42, where each successive view 30 is positioned and oriented according to running need, as shown in FIG. 9A. The user may want a running map 72 which is continuously updated as the endoscopic space is explored. Such a map 72 would evolve as the user covers increasingly more area. This would be in cases where one would want to keep track of bleeding or other dynamic physiological effects. As shown in FIG. 9B, sections of the map 72 corresponding to parts of the anatomy not yet covered 74 would be blank, and sections of the map corresponding to parts of the anatomy inspected previously 76 would gradually fade, similar to the phenomenon of persistence on oscilloscopes. A solid line indicates the current frame 30, and the line thickness indicates the time elapsed since a frame was captured. The frame-indexing array would store the position, orientation, and time of each random capture and this information would be used to synthesize and display a group of random frames with random orientations in an organized and meaningful way, for example with aligned view orientations. The user may also want to generate a map based on information already achieved during such a random manual scan. In this case the system would automatically patch gaps or blank areas by point to point motion and capture determined by standard search algorithms applied to a frame-indexing array.

Figure 10B:
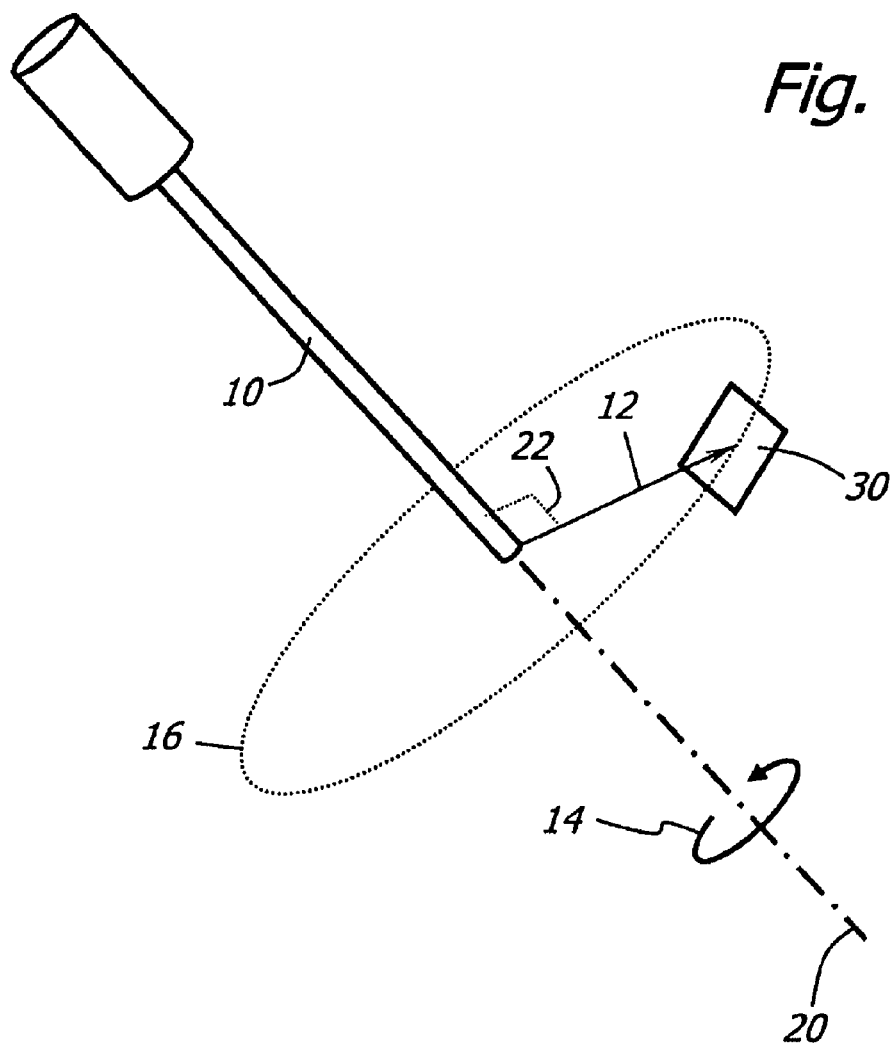

The method of the present invention also applies to endoscopes which do not have a variable direction of view. Depending on the particular anatomy and the endoscopic field of view, most any endoscope can provide wide systematic coverage if controlled appropriately. As shown in FIG. 10A, connecting endoscopes to a robotic arm 78 such as the Automated Endoscopic System for Optimal Positioning (AESOP) described in U.S. Pat. No. 5,524,180 to Wang et al. can be used for endoscopic map-building because it makes it possible to keep track of the position of new 80 and previous views 82, 84. Also, endoscopes with a fixed off-axis viewing direction can be instrumented with electromechanical control of their orbital axis, as seen in FIG. 10B. As such a scope 10 rotates about its own axis 20, its field of view 30 sweeps out a panoramic band, and depending on the angle of the viewing direction, the field of view, and the geometry of the anatomy, it will in some cases be possible to cover large areas. With an appropriate sensing system, the method of the present invention could also be applied to flexible endoscopes.

It is also possible to build endoscopic maps by manually controlling an image guided endoscope 10 with a fixed viewing direction, as shown in FIG. 11. An image guidance system 86 tracks the position of the endoscope 10 relative to an anatomical structure 52 and displays its real-time view field 80 and previous view fields 82, 84 relative to a computer graphical representation of the endoscope 88, its view 89, and the anatomical structure 90. With this visual position feedback, the user can then manipulate the endoscope 10 to "paint" the inside of the anatomical model 90 until it is completely covered. The "paint" can be either a texture map from the endoscopic video stream or more simply a highlighting color to show which areas have been covered.

A graphical user interface 88 for the endoscopic mapping system of the present invention is shown in FIG. 12. This interface includes a set of buttons for performing endoscopic navigation and mapping tasks. Both a live endoscopic view 30 and a global endoscopic map 72 are displayed. The display configuration is versatile such that a user could fill the whole display area with the map 72 in place of the current endoscopic view 30 if desired. For purposes of navigation and orientation, a small window 94 provides graphical representations of the endoscope 88, its view 89, and scan line trajectories 96. This phantom could be replaced by an actual 3D anatomical model 86 based on volumetric scan data from a radiography or an MRI in cases when such information is available.

The present invention has been described above in terms of a presently preferred embodiment so that an understanding of the present invention can be conveyed. However, there are many variations not specifically described herein but with which the present invention is applicable. For example, while the examples were given with respect to an endoscope for use in surgical procedures, the present invention would be equally applicable with respect to a borescope for use within various mechanical structures. Also, there are many different endoscopic scan patterns which could be used to produce omniramas, and these patterns might vary with application. The scope of the present invention should therefore not be limited by the embodiments illustrated, but rather it should be understood that the present invention has wide applicability with respect to viewing instruments and procedures generally. All modifications, variations, or equivalent elements and implementations that are within the scope of the appended claims should therefore be considered within the scope of the invention.

What is claimed is:

1. A method of obtaining endoscopic maps with an endoscope having a longitudinal axis and a view vector with an attendant view that pivots relative to the longitudinal axis of the endoscope, the method comprising:
    programming a scan trajectory along which the view vector moves relative to the longitudinal axis of the endoscope to provide a predefined sequence of overlapping views of a surface;
    capturing a sequence of overlapping images corresponding to the predefined sequence of overlapping views as the view vector moves along the scan trajectory;
    associating a set of configuration coordinates with each of the captured images;
    using the captured images and the configuration coordinates associated therewith to create a map of the surface larger than the view that attends the view vector; and
    selecting a location on the map and automatically moving the view vector to an orientation of the view vector when an image corresponding to the location was captured.

2. A method of obtaining endoscopic maps with an endoscope having a longitudinal axis and a view vector with an attendant view that pivots relative to the longitudinal axis of the endoscope, the method comprising:
    providing a scan trajectory along which the view vector moves relative to the longitudinal axis of the endoscope to provide a predefined sequence of views of a surface;
    capturing a sequence of images corresponding to the predefined sequence of views as the view vector moves along the scan trajectory;
    associating a set of configuration coordinates with each of the captured images;
    using the captured images and the configuration coordinates associated therewith to create a map of the surface larger than the view that attends the view vector; and
    in response to a selection of a location on the map, automatically moving the view vector to an orientation of the view vector when an image corresponding to the location was captured.

3. The method of claim 2, wherein the view vector has three degrees of freedom and the configuration coordinates associated with each of the captured images represents the orientation of the view vector with respect to the three degrees of freedom.

4. The method of claim 2, wherein the view vector moves along the scan trajectory at a speed that is adjustable.

5. The method of claim 2, wherein the configuration coordinates are stored in a frame-indexing array that correlates image information with viewing position.

6. The method of claim 5, wherein the orientation of the view vector is known relative to the direction of gravity as the view vector moves along the scan trajectory.

7. The method of claim 2, wherein portions of the map fade in brightness as the time elapsing since the capture of the images corresponding to those portions increases.

8. The method of claim 2, wherein, for each of the views for which an image is captured, at least two separate images of the view are captured and combined into a compound image of higher quality than the separate images.

9. A method of obtaining endoscopic maps with an endoscope having a longitudinal axis and a view vector with a field of view that pivots relative to the longitudinal axis of the endoscope, the method comprising:
    scanning a surface with the view vector, the view vector moving along a scan trajectory relative to the longitudinal axis of the endoscope;
    capturing a sequence of images of the surface as the view vector moves along the scan trajectory;
    associating a set of configuration coordinates with a set of the captured images;
    using at least a subset of the set of the captured images and the configuration coordinates associated therewith to create a map of the surface larger than the field of view; and
    in response to a selection of a location on the map, automatically moving the view vector to an orientation of the view vector when an image corresponding to the location was captured.

10. The method of claim 9, wherein the view vector has three degrees of freedom and the configuration coordinates associated with the set of the captured images represents the orientation of the view vector with respect to the three degrees of freedom.

11. The method of claim 9, wherein the map comprises a mosaic of the overlapping images.

12. The method of claim 9, wherein the view vector moves along the scan trajectory at a speed that is adjustable.

13. The method of claim 9, wherein the configuration coordinates are stored in a frame-indexing array that correlates image information with viewing position.

14. The method of claim 13, wherein the orientation of the view vector is known relative to the direction of gravity as the view vector moves along the scan trajectory.

15. The method of claim 9, wherein the scan trajectory is a spiraling path.

16. The method of claim 9, wherein the scan trajectory is circular.

17. The method of claim 9, wherein the scan trajectory is a first scan trajectory, the method further comprising the steps of:
providing a second scan trajectory along which the view vector moves relative to the longitudinal axis of the endoscope to provide a predefined sequence of overlapping views of the surface;
capturing a sequence of overlapping images corresponding to the predefined sequence of overlapping views as the view vector moves along the second scan trajectory; and
associating a second set of configuration coordinates with a set of the images captured as the view vector moves along the second scan trajectory;
wherein the map of the surface is created using at least a subset of the captured images from the first and second scan trajectories.

18. The method of claim 9, wherein portions of the map fade in brightness as the time elapsing since the capture of the images corresponding to those portions increases.

19. The method of claim 9, wherein, for each of a set of views for which an image is captured, at least two separate images of the view are captured and combined into a compound image of higher quality than the separate images.

20. The method of claim 9, wherein the capturing step comprises capturing a sequence of overlapping images of the surface as the view vector moves along the scan trajectory.

21. A system comprising:
a computer;
an endoscope having a longitudinal axis and a view vector having a field of view that pivots relative to the longitudinal axis of the endoscope, the computer configured to move the view vector along a scan trajectory relative to the longitudinal axis of the endoscope; and
an image capture device configured to capture a plurality of images of a surface as the view vector moves along the scan trajectory, the computer configured to associate a set of the plurality of images with a set of configuration coordinates,
wherein the computer uses at least a subset of the set of images and the configuration coordinates associated therewith to create a map of the surface larger than the field of view, and in response to a selection of a location on the map, the computer automatically moves the view vector to an orientation of the view vector when an image corresponding to the location was captured.

* * * * *